United States Patent [19]
Haber et al.

[11] Patent Number: 5,279,606
[45] Date of Patent: Jan. 18, 1994

[54] NON-REACTIVE COMPOSITE SEALING BARRIER

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 750,576

[22] Filed: Aug. 28, 1991

[51] Int. Cl.$^5$ .............................. B65D 85/00
[52] U.S. Cl. ...................... 604/403; 215/DIG. 3; 215/364
[58] Field of Search ............ 604/403, 415, 416, 410; 215/DIG.; 206/438

[56] References Cited

U.S. PATENT DOCUMENTS

| | | | |
|---|---|---|---|
| 2,649,090 | 8/1953 | Parsons et al. | 604/415 |
| 3,198,368 | 8/1965 | Kirkland et al. | 215/DIG. 3 X |
| 3,313,439 | 4/1967 | Robinson | 604/415 X |
| 3,552,591 | 1/1971 | Wimmer | 215/DIG. 3 UX |
| 3,760,969 | 9/1973 | Shimamoto et al. | 215/DIG. 3 X |
| 4,569,457 | 2/1986 | Hatakeyama et al. | 215/364 |
| 4,614,276 | 9/1986 | Ihara et al. | 215/364 |
| 4,915,243 | 4/1990 | Tatsumi et al. | 215/364 X |
| 4,973,504 | 11/1990 | Romberg et al. | 215/364 X |
| 5,114,411 | 5/1992 | Haber et al. | 604/203 |

Primary Examiner—Robert A. Hafer
Assistant Examiner—Sam Rimell
Attorney, Agent, or Firm—Townsend and Townsend Khourie and Crew

[57] ABSTRACT

An elastomeric pharmaceutical barrier (2, 50, 75, 100) formed as a piston, a stopper, or a cap-like gasket and diaphragm structure for use in pharmaceutical containers such as vials, syringes, cartridges and the like. The barrier combines a main body (4, 52, 76, 102) of butyl or silicone based rubber to provide a fluid seal mechanism and includes a pharmaceutically inert insert (6, 54, 78, 104) which provides a substantial portion (40, 68, 92, 130) of a surface of the barrier to be exposed to the pharmaceutical. The non-reactive insert can be fabricated from polytetrafluoroethylene, glass, stainless steel or ceramic material and reduces the surface area of rubber exposed to pharmaceutical contact, therefore making the applicable face of the barrier substantially inert and nonreactive to the contacting pharmaceutical. The insert can be made to incorporate a guide (62, 66) and channel (64) for needle canula (74) access as well as a pressure valve system (118, 126, 132, 136) to allow fluid flow through the barrier structure.

18 Claims, 6 Drawing Sheets

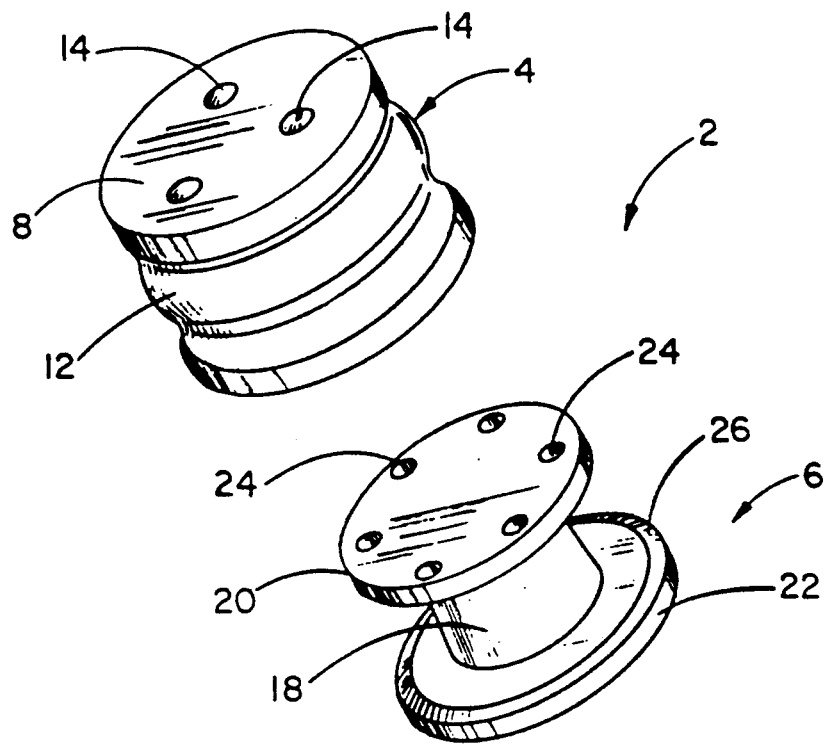
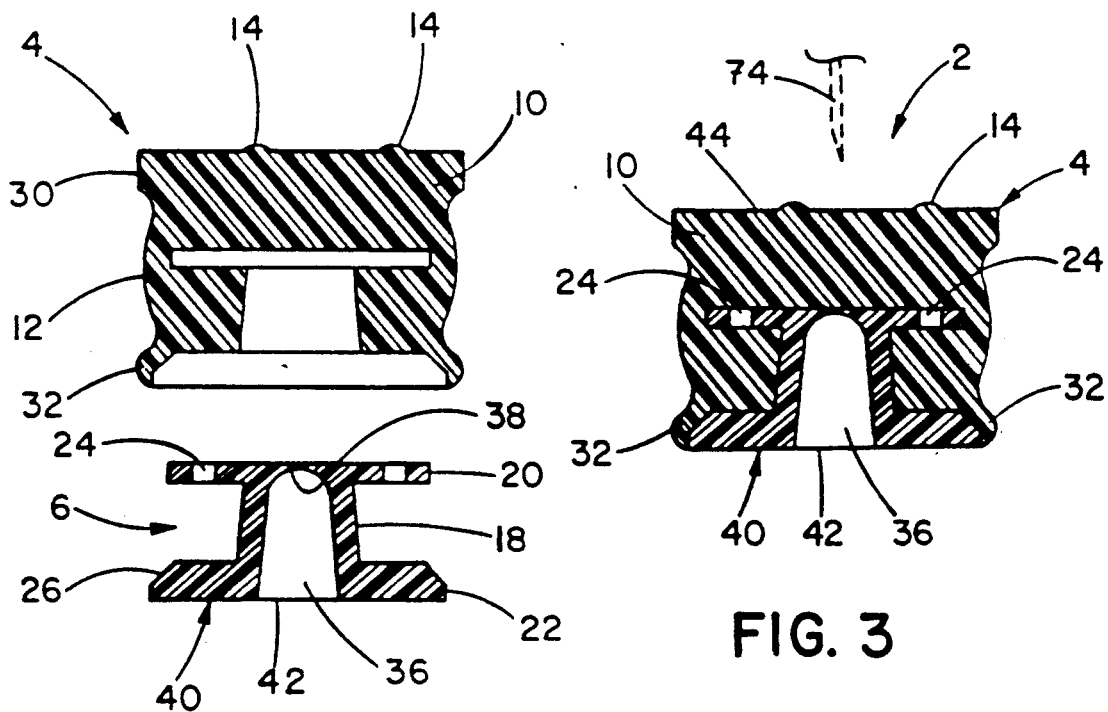
FIG. 1
FIG. 2
FIG. 3

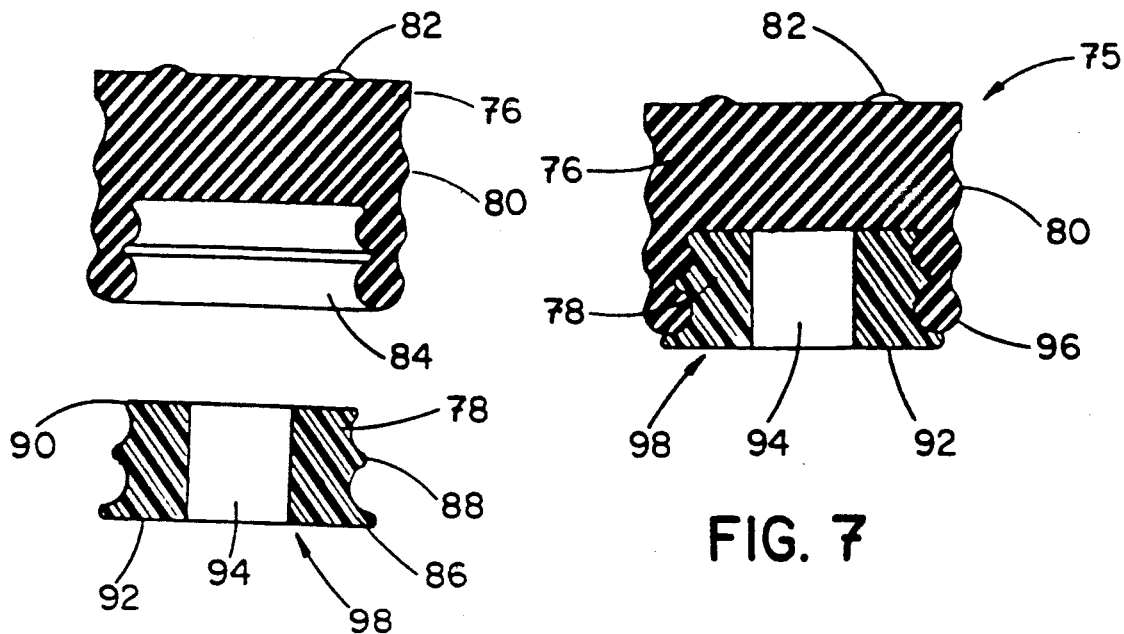
FIG. 6
FIG. 7
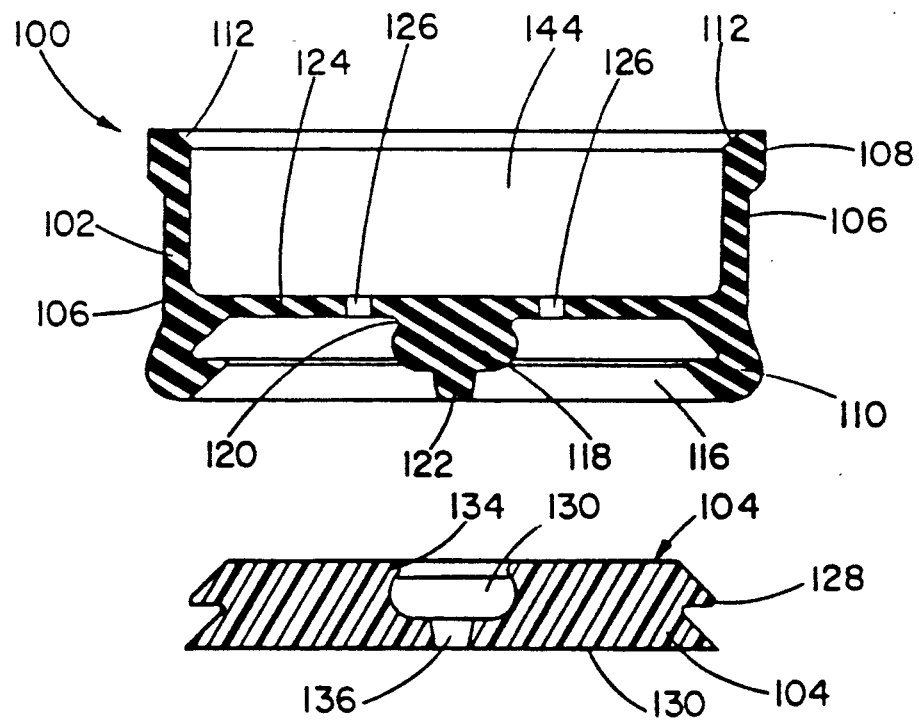
FIG. 8

NON-REACTIVE COMPOSITE SEALING BARRIER

BACKGROUND OF THE INVENTION

Various butyl rubber formulations have been molded into several forms of elastomeric sealing barriers such as stoppers, diaphragms and pistons for pharmaceutical containers including vials, cartridges, syringes and the like. Butyl rubber barriers are desirable in these applications due to their good elasticity, moldability, inertness and consequent non-reactivity when placed in prolonged contact with pharmaceuticals. Most, if not all, butyl rubber formulations, however, require a silicone lubricant coating to ensure ease of axial movement within rigid structures such as syringes, cartridges, or the like. Alternatively, silicone-based rubber compounds such as SILASTIC ® (registered trademark of Dow Corning Corporation) can be employed to provide some degree of lubricity.

Regardless of whether silicone is used in the rubber compound or as a secondary lubricant, silicone can compromise the purity of many surrounding pharmaceuticals due to possible reaction with and/or contamination of the pharmaceuticals housed in the relevant container when stored for long periods of time. Therefore, rigid containers such as cartridges which use conventional silicone-based sealing barriers cannot be safely used for long term storage with many pharmaceuticals.

For this reason, coating processes for coating rubber with non-reactive materials such as polytetrafluoroethylene available as TEFLON ® (registered trademark of Dupont Corp.) have been developed. TEFLON ® coating is desirable due to its low friction surface and inertness, but presents fabrication problems for some structures.

With conventional technology, TEFLON ® may not be applied to typical resilient sealing pistons or stoppers, due to their non-flat configuration and thermal expansion. Therefore, coating a conventional elastomeric sealing stopper with TEFLON ® rather than silicone is not a practical alternative.

SUMMARY OF THE INVENTION

The present invention is directed to a pharmaceutically inert composite sealing barrier for use in pharmaceutical containers such as cartridges, syringes and vials. The barrier can take the form of a piston, stopper, gasket or diaphragm appropriate for the particular sealing application. The barrier has the sealing advantages of butyl rubber formulations or silicone-based materials, but minimizes the surface area of the resident silicone which could potentially interact with a contacting pharmaceutical.

Regardless of the form, the barrier uses a silicone-based or coated resilient main body which acts as a fluid seal mechanism and includes a pharmaceutically inert insert or core which at least partially provides an outer surface of the barrier. An outer surface of the non-reactive insert is positioned in the container so that it faces the critical pharmaceutical and therefore minimizes the surface area of silicone material exposed to the pharmaceutical without compromising the sealing characteristics of the device.

The invention, when taking the form of a piston, uses a pharmaceutically inert insert disposed at one end of the piston which provides the majority of the outer surface of that end. In the form of a stopper, the main body of the sealing barrier is preferably injection molded around a pharmaceutically inert core. The core can be configured to include a channel which allows penetration of a needle canula through the main body for access to the pharmaceutical when the device is sealing a chamber in a rigid container.

When the invention is employed in more complex containers such as dual-chamber vials, the barrier may take the form of a gasket and diaphragm structure. In such a form, the sealing mechanism is preferably formed with a butyl rubber or SILASTIC ® main body having a pharmaceutically inert insert which provides the majority of the surface area exposed to the critical pharmaceutical. Alternatively, the device can also be formed with a releasable plug in a flow path through the device to provide a secure sealing mechanism having a pressure valve mechanism which can be activated to allow liquid or gaseous flow through the structure.

SILASTIC ® is preferably used for construction of the main body regardless of form. Butyl rubber can also be used with a silicon lubricant coating to provide sealing and facilitate axial movement within a rigid container. The non-reactive insert is preferably manufactured from a suitable pharmaceutically inert material such as TEFLON ®, glass or ceramic.

BRIEF DESCRIPTION OF THE DRAWINGS

FIG. 1 is an exploded isometric view of the preferred embodiment of the invention formed as a piston with the pharmaceutically inert core shown separated from the elastomeric main body.

FIG. 2 is a cross-sectional side view of the device shown in FIG. 1 illustrating the elastomeric main body above and separated from the non-reactive insert.

FIG. 3 is a cross-sectional side view of the device shown in FIG. 2 in the unitary condition showing the non-reactive core disposed within the elastomeric piston body.

FIG. 6 is a cross-sectional side view of another alternative embodiment of the invention formed as a stopper or piston having an elastomeric main body and a non-reactive insert in the separated condition, the insert having a centralized hollow channel.

FIG. 7 shows the embodiment of FIG. 6 with the main body and insert in an assembled condition.

FIG. 8 is a cross-sectional side view of an alternative embodiment of the invention forming a gasket and diaphragm structure with an elastomeric main body and plug shown separated from the non-reactive insert.

FIG. 10A illustrates the device of FIG. 10 with the diaphragm and plug components displaced from the cavity to allow passage of liquid or gaseous flow through the barrier structure.

DESCRIPTION OF THE PREFERRED EMBODIMENT

Figure 4:
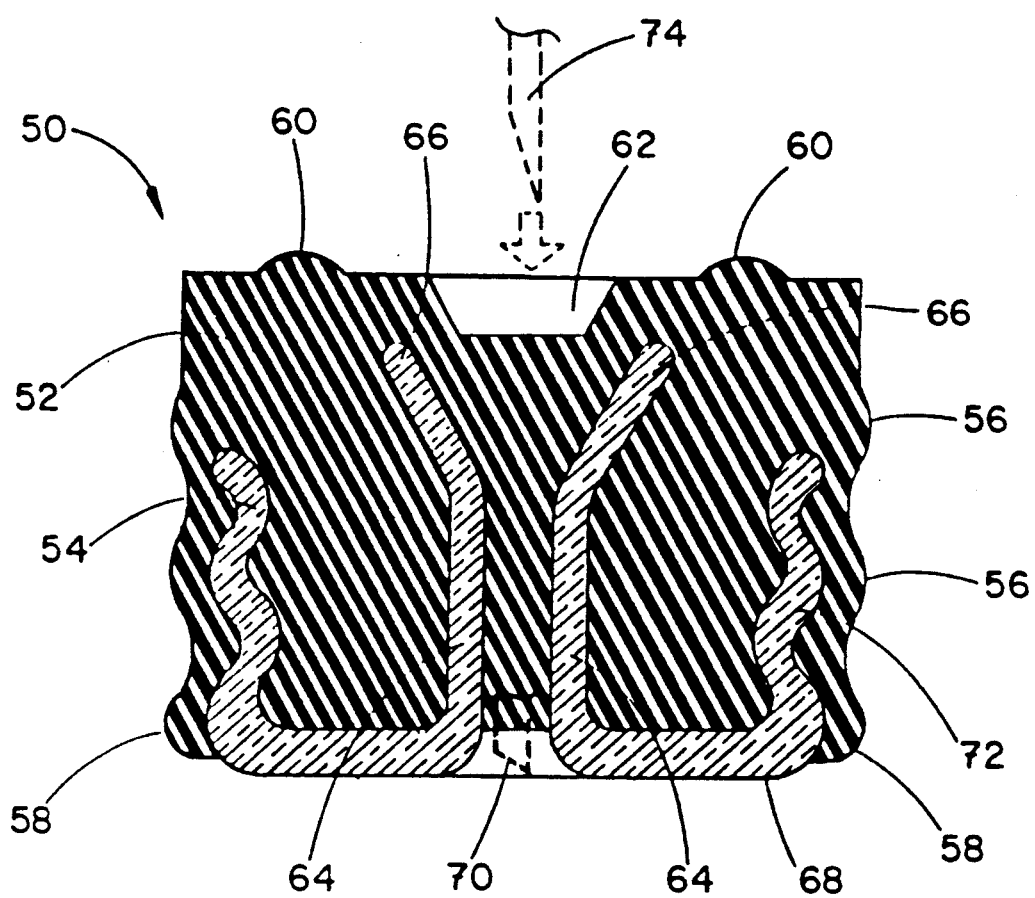
FIG. 4 is a cross-sectional side view of an alternative embodiment of the invention formed as a stopper having a pharmaceutically inert insert molded into the stopper body and providing a needle canula guide channel to allow needle access through the stopper.

Referring to FIGS. 1-3, sealing barrier 2 is shown in the preferred embodiment formed as a piston 10 comprising main body 4 and inert member 6. Main body 4 is elastomeric and made cylindrical in shape with appropriate dimensions for insertion into the particular syringe, cartridge, vial or the like. Main body 4 includes sealing ridge 12 about its periphery to provide sufficient sealing against a chamber wall (not shown) which would abut the external surface of main body 4. A plurality of protrusions 14 are included on upper side 8 of main body 4 to prevent sticking to flat surfaces, or when packed for shipping or storage, sticking to other sealing barriers.

In the preferred embodiment, main body 4 of piston 10 is formed of a heat-stable silicone compound such as SILASTIC ® (a registered trademark of Dow Corning Corporation) and is molded around inert member 6. Inert member 6 comprises central hub 18, upper rim 20 and lower rim 22. Upper rim 20 includes multiple bonding channels 24 which allow flow through of the SILASTIC ® material during the molding process to mechanically bond inert member 6 with main body 4 to make an integral unit.

Now referring to FIG. 2, the device illustrated in FIG. 1 is shown in cross section with main body 4 and inert member 6 separated. Main body 4, formed as piston 10, has an outer side perimeter surface which includes sealing ridge 12, sealing edge 30 and sealing lip 32. This configuration allows maximum sealing against a cylindrical rigid body during thermal expansion and contraction while allowing for axial movement within the rigid body without compromising the seal.

The cross section illustrated in FIG. 2 shows molding cavity 34 which is occupied by inert member 6 when main body 4 and inert member 6 are made integral. Inert member 6 is preferably made of materials which are non-reactive to most pharmaceuticals. The preferred material is polytetrafluoroethylene (PTFE) which is available under the trademark TEFLON ® (a registered trademark of the Dupont Company, Wilmington, Del.). Other suitable pharmaceutically inert materials include low alkaline glass, ceramics, and stainless steel. Inert member 6 includes hollow 36 which extends through central hub 18 and into upper rim 20. Hollow 36 terminates at a thin walled ceiling 38 and has open end 42. Hollow 36 allows inert member 6 to be constructed using a minimal amount of materials while providing a structure which can be pierced by a needle cannula 74 (see FIG. 3) to allow access to a pharmaceutical through the device if necessary.

Now referring to FIG. 3, main body 4 and inert member 6 are shown in an integral, unibody construction. Molding of piston 10 about inert member 6 allows resilient rubber material to flow into bonding channels 24 to help secure inert member 6 within main body 4 during thermal expansion and contraction. In the molded, unibody condition, inert member 6 provides all but a small portion of the surface area of lower surface 40. As such, lower surface 40 is substantially non-reactive with pharmaceuticals when exposed to the same. When piston 10 is retained within a cylindrical channel such as a pharmaceutical cartridge, only a small portion of sealing lip 32 is exposed to pharmaceutical when the pharmaceutical is in communication with lower surface 40.

Referring now to FIG. 4, an alternative embodiment of the invention is shown. In this embodiment, sealing barrier 50 functions as either a stopper or a piston. Sealing barrier 50 includes main body 52 and inert member 54. In this embodiment, main body 52 is fabricated from elastomeric materials as previously described, and inert member 54 is made of glass or other materials consistent with that discussed in the preferred embodiment above.

Main body 52 is preferably molded around inert member 54. Main body 52 is generally cylindrical in shape, and configured to perform a sealing function. Main body 52 therefore includes a plurality of sealing ridges 56 about its periphery. Preferably, three sealing ridges are used as shown FIG. 4; however, a larger or lesser number could be employed. Main body 52 includes protrusions 60 and sealing lip 58 as previously described with protrusions 14 and sealing lip 32 above. Main body 52 also includes a centrally located recess 62 used to provide access by needle canula 74 as will be described below.

Inert member 54 is configured to include a cylindrically shaped needle channel 64 which flares out near the upper end to form channel guide 66. Channel guide 66 is positioned below recess 62. Inert member 54 also includes lower surface 68 and ribbed skirt 72. Ribbed skirt 72 is made nonlinear to provide maximum surface area and a surface contour to enhance mechanical bonding with main body 52.

This embodiment of the invention assists ease of use with a needle canula for access to a pharmaceutical or other liquid through the device. Needle canula 74, indicated by broken lines, can be aligned above recess 62 and forced through main body 52 along needle channel 64. Channel guide 66 deflects and directs needle canula 74 into channel guide 66 if inserted into main body 52 off-axis or off-center. This structure facilitates needle canula access through main body 52 and inert member 54.

Figure 5:
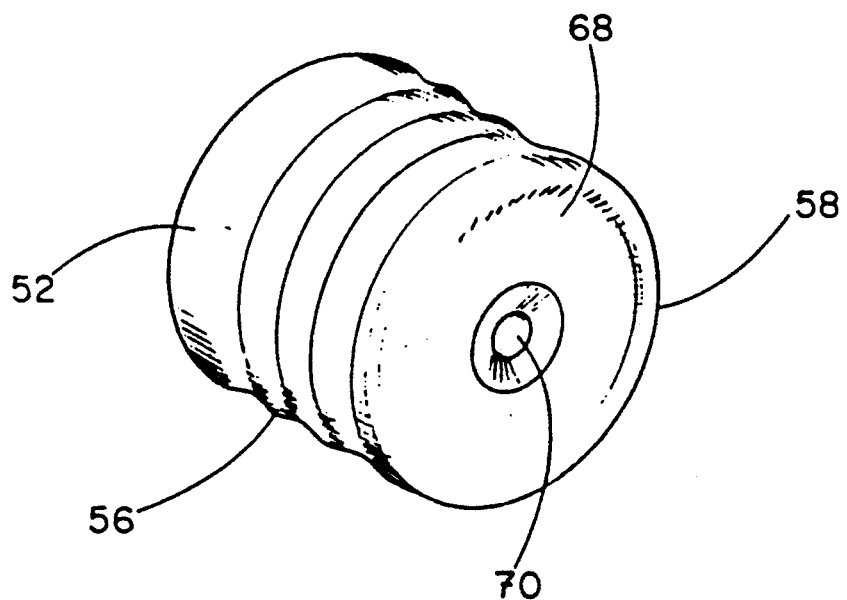
FIG. 5 is a perspective view of the device shown in FIG. 4 illustrating the face of the non-reactive insert forming the majority of the surface area to be exposed to an applicable pharmaceutical.

Referring now to FIG. 5, the device shown in FIG. 4 is illustrated to show lower surface 68 of inert member 54. As is illustrated, lower surface 68 of inert member 54 provides the majority of exposed surface area on this side of the device. As such, lower surface 68 would be positioned adjacent the critical pharmaceutical in the particular application. Void 70 is formed within the longitudinal axis of needle channel 64 near lower surface 68 where the elastomeric material of main body 52 extends into needle channel 64. Void 70 acts to allow fluid to migrate unrestricted to a needle cannula 71 projecting into void 70 (as indicated in phantom).

Referring now to FIGS. 6 and 7, another alternative embodiment of the invention is shown. In this embodiment, sealing barrier 75 is comprised of main body 76 and removable inert insert 78. Main body 76 and insert 78 can be molded together or fabricated separately and assembled. Inert insert 78 can be secured into main body 76 and retained in cavity 84. Construction of main body 76 is consistent with the embodiments previously described in that it has protrusions 82 and sealing ridge 80. Inert insert 78 is formed cylindrical in shape and having lower rib 86, radial retention rib 88, and upper rib 90. These ribs correspond to the receiving configuration of cavity 84 to allow insert 78 to be securely retained within main body 76 as depicted in FIG. 7. When coupled together, main body 76 and inert insert 78 form a composite device wherein lower surface 98 provides a substantially non-reactive outer surface on the lower side of the device. Lower rib 86 abuts, and is external to, sealing lip 96 as shown to maximize external non-reactive surface area. Hollow 94 facilitates needle canula access through main body 76 and inert insert 78 or allow physical displacement of an object into hollow 94.

Figure 9:
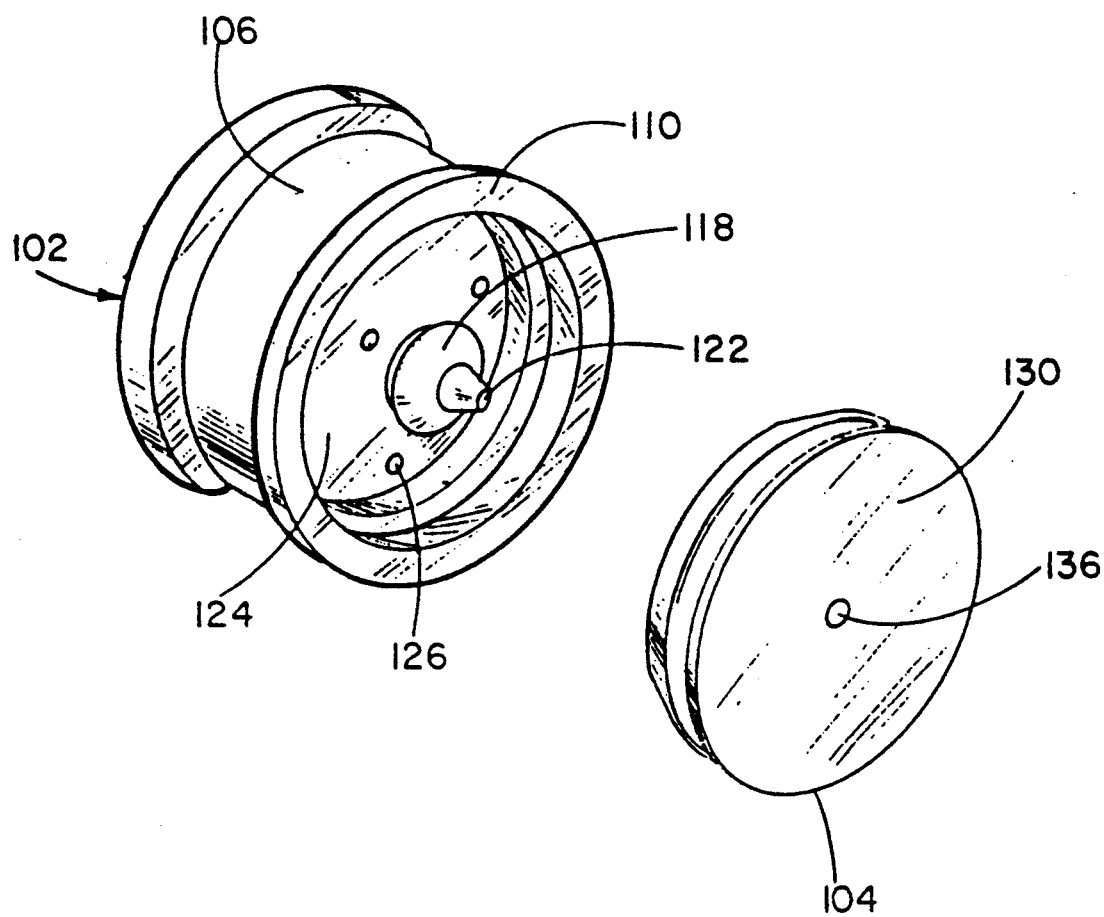
FIG. 9 is a perspective view of the elastomeric gasket and diaphragm structure illustrated in FIG. 8 showing flow apertures disposed in the diaphragm.
Figure 10:
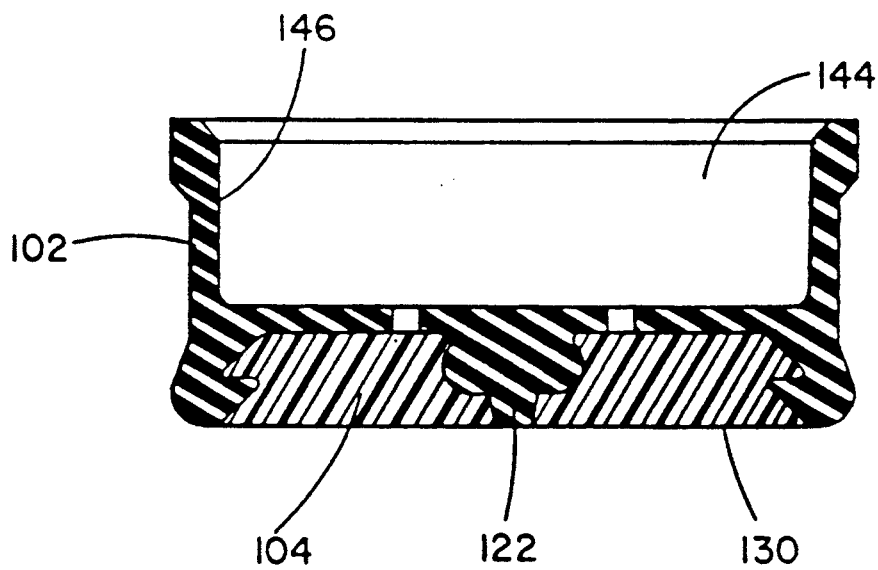
FIG. 10 a cross-sectional side view of the device illustrated in FIG. 8 shown in the assembled condition with the non-reactive insert disposed within the elastomeric body with the depending plug retained within the insert cavity to provide a structure for a fluid-tight seal.
Figure 10:
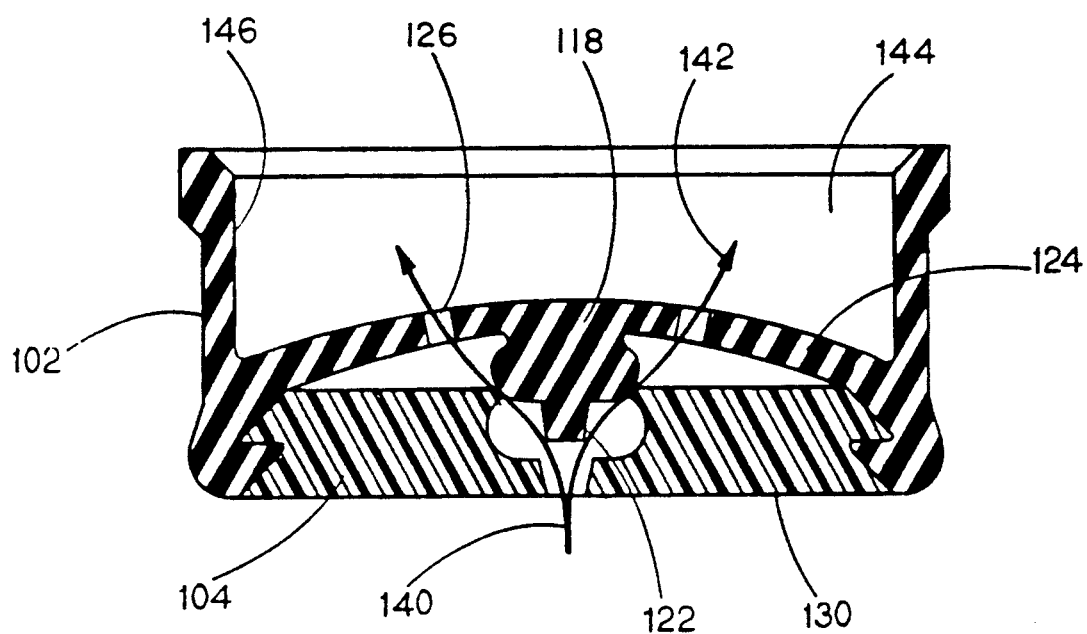

In a further alternative embodiment of the invention, the device can be formed as shown in FIGS. 8–10. Sealing barrier 100 in this embodiment is configured to provide an elastomeric gasket sealing mechanism between two rigid bodies while additionally providing a pressure valve flow-through mechanism to allow fluid flow through the device. Sealing barrier 100 includes main body 102 and inert insert 104. Main body 102 and inert insert 104 are made of materials consistent with those previously described. Main body 102 is made generally cylindrical in shape, having side walls 106 terminating at upper lip 108 and sealing lip 110. These surfaces would provide sealing contact with the internal wall of a cylindrical chamber which will be more fully described below. Wall set-back 114 is used to facilitate insertion of sealing barrier 100 into the inner diameter of a container using an assembly technique commonly referred to as the cork and wine bottle procedure well known in the art. A second, rigid cylindrical container member can be inserted into inside chamber 144 as will also be more fully described below. Chamfer 112 allows frictional insertion and engagement of such a container within inside chamber 144.

Continuing with the description of main body 102, diaphragm 124 is disposed across main body 102 extending out from side wall 106. Three flow channels 126 are provided in diaphragm 124. Located below diaphragm 124 is cavity 116 for receiving inert insert 104. Bulb plug 118 downwardly extends from diaphragm 124 and includes collar 120 and face 122. FIG. 8 illustrates a cross-section of inert insert 104 including radial retention rib 128 for engagement in cavity 116. Insert 104 includes lower surface 130 and plug seat 132.

Referring now to FIG. 9, a cross-sectional view of the device illustrated in FIG. 8 is shown. As can be seen by the illustration, flow channels 126 are disposed within diaphragm 124 around bulb plug 118. The drawing suggests 3 evenly spaced flow channels 126; however, any number of flow channels can be used.

Main body 102 and inert insert 104 are shown in FIG. 10 in the coupled configuration. Plug seat 132 receives bulb plug 118 and face 122 extends down through valve orifice 136. Radial retention rib 128 helps retain inert insert 104 within main body 102. In the fully engaged condition, main body 102 and inert insert 104 provide an effective sealing mechanism that can withstand thermal expansion and contraction. In the engaged condition, bulb plug 118 is retained within plug seat 132 and secured therein by collar ring 134 abutting collar 120 of plug 118. Plug 118 can be dislodged from plug seat 132 by introducing sufficient pressure along lower surface 130. Pressure, indicated by arrow 140, pushes upon face 122 to dislodge bulb plug 118 from plug seat 132. In the dislodged condition, indicated by broken lines, valve orifice 136 provides fluid access through inert insert 104 into plug seat 132. Fluid can continue to flow through flow channels 126, thereby providing flow access to inside chamber 144. The configuration of this embodiment, therefore, provides an effective valve mechanism integral with sealing barrier 100.

Figure 11:
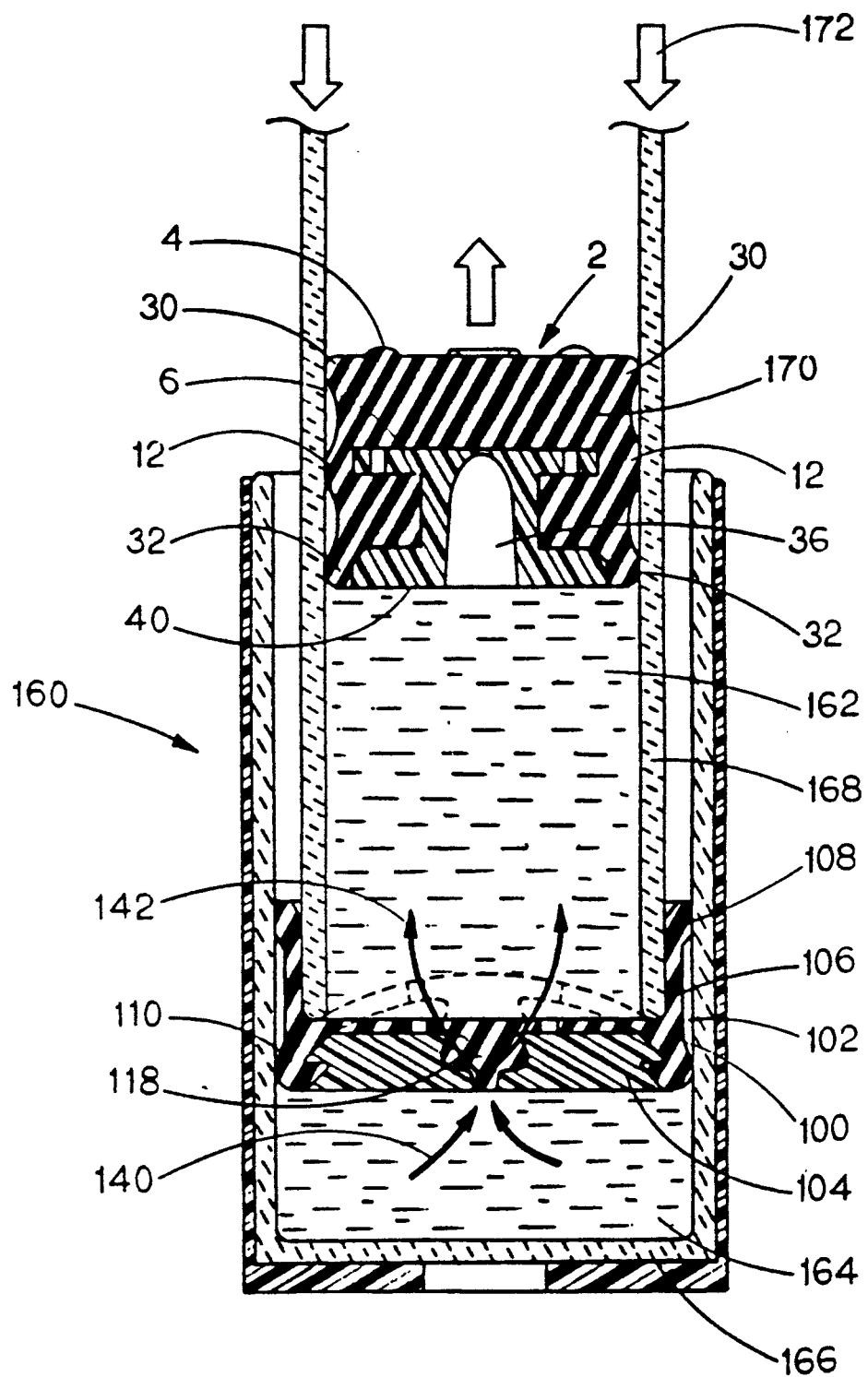
FIG. 11 is a cross-sectional side view of an example dual-chamber vial system incorporating the devices illustrated in FIG. 3 and FIG. 10.

Referring now to FIG. 11, the alternative embodiment just described is shown employed in an example two-chamber vial system. This dual-chamber vial system is more fully described in U.S. patent application Ser. No. 07/615,610, entitled Multi-Chamber Vial and filed on Nov. 19, 1990, now U.S. Pat. No. 5,114,411 and in U.S. patent application Ser. No. 07/741,780, entitled Mixing Vial and filed on Aug. 7, 1991, now U.S. Pat. No. 5,188,615 the disclosures of which are incorporated by reference. The reference to these applications is made for discussion purposes only and is not intended to limit the application of the disclosed invention. The device illustrated in FIG. 11 is intended merely to facilitate explanation of one possible application of applicant's invention and it by no means limits the application thereto.

In FIG. 11, two-chamber vial 160 is shown having dual chambers, a first chamber 162 and second chamber 164. The function of such a device is to separate the contents of first chamber 162 and second chamber 164 for storage purposes and allow automatic mixing of the two components when necessary. Second chamber 164 is provided by cylindrical container 166 and sealing barrier 100. Inert insert 104 retains bulb plug 118 to provide an effective fluid-tight sealing barrier which is axially positionable within cylindrical chamber 166. Sealing lip 110 and upper lip 108 abuts the inside surface of cylindrical container 166 as shown. Main body 102 receives inner container 168 by frictional engagement along inside wall 146 and seat 148. Sealing barrier 100 therefore provides a gasket sealing mechanism between cylindrical container 166 and inner container 168.

First chamber 162 is further defined by sealing barrier 170. Sealing barrier 170 can take the form of any of the embodiments described, but is shown illustrated in the first, preferred embodiment formed as piston 2. Main body 4 is disposed within inner container 168 such that lower surface 40 of inert member 6 faces the pharmaceutical contained in first chamber 162. Sealing ridge 12, sealing edge 30 and sealing ridge 32 abut the inner surface of inner container and allow axial movement along that surface.

To mix the component resident in first chamber 162 and second chamber 164 together, the valve mechanism of sealing barrier 100 is activated. In two-vial container 160 illustrated in FIG. 11, this can be accomplished by inflicting relative downward pressure illustrated by arrows 172 which forces sealing barrier 100 in an axial direction downwardly thereby increasing the pressure within second chamber 164. Pressure increases until sufficient to dislodge plug 118 from plug seat 132, thereby allowing fluid flow 140 through sealing barrier 100 into first chamber 162 shown as channeled flow 142 to mix the components together. Other containers can benefit from the sealing barriers of applicant's invention in similar fashion.

The foregoing description of the preferred and alternative embodiments of the invention have been presented for purposes of illustration and description. It is not intended to be exhaustive or to limit the invention to the precise form disclosed, and obviously many modifications and variations are possible in light of the above teaching. For example, the alternative forms of the invention could be employed in a variety of rigid containers and need not be cylindrical in shape. Other shapes, such as octagon, square or rectangular crosssections could be employed without materially altering the features of the invention. Also, modification to the constructions can be employed. Barrier 100 could be modified to have insert 104 facing the opposite direction by positioning within inside chamber 144. Additionally, a wide range of rubber formulations which provide suitable sealing characteristics can be employed. The embodiments chosen and described in this description are, however, selected to best explain the principles of the invention and the invention's practical application to thereby enable others skilled in the art to best utilize the invention in various embodiments and/or dimensions with various modifications as are suited to the particular use contemplated. It is intended that the scope of this invention be defined by the claims appended hereto.

What is claimed is:

1. An elastomeric sealing barrier, comprising a resilient main body, said entire main body having a generally cylindrical shape, a pharmaceutically inert member which forms at least a portion of a surface of said barrier, a cavity formed in the main body for receiving and retaining the entire inert member within the main body, and interlock means for mechanically securing the inert member within the cavity.

2. The barrier of claim 1 wherein said main body is configured to form a piston, said piston having a first surface, a second surface and a perimeter wall coupling the first and second surfaces, said perimeter wall further comprising a sealing surface.

3. The barrier of claim 1 wherein said inert member is constructed of a material selected from the group of polytetrafluoroethylene, ceramic, glass and stainless steel.

4. The barrier of claim 1 wherein said main body is constructed of silicone-based rubber material.

5. The barrier of claim 1 wherein the interlock means includes a radially outwardly extending rim on the inert member.

6. The barrier of claim 1 wherein said inert member further comprises a hollow interior having an open end and a closed end, said closed end being piercable by a needle cannula.

7. The barrier of claim 1 wherein said inert member further comprises a bore through said inert number, the bore configured to allow a needle cannula to penetrate through said bore.

8. The barrier of claim 1 wherein said inert member is molded into said main body, said inert member further comprising a guide channel to allow access of a needle cannula through said barrier.

9. An elastomeric sealing barrier, comprising a resilient main body, a pharmaceutically inert member which forms at least a portion of a surface of said barrier, and a pressure valve activatable by a pressure differential applied between said first side and said second side of said body.

10. The barrier of claim 9 wherein said pressure valve comprises a receptacle formed in said inert member and a plug removably positioned in the receptacle.

11. The barrier of claim 10 wherein said plug is made integral with said body.

12. The barrier of claim 11 wherein said inert member defines said receptacle for receiving said plug, said plug being movable between a first position, positioned within said receptacle, and a second position, positioned at least partially external of said receptacle, said first position preventing fluid from passing through said barrier, said second position allowing fluid to pass through the barrier.

13. An elastomeric sealing barrier, comprising a resilient main body and a pharmaceutically inert member which forms at least a portion of a surface of said barrier, said body being made of silicone-based rubber material, and configured to form a gasket, said body further comprising:
    a perimeter wall, said perimeter wall having a sealing ridge configured to provide a fluid tight gasket seal between two adjacent rigid surfaces;
    a diaphragm disposed across said perimeter wall, said diaphragm including a flow aperture and a protruding plug; and
    a cavity formed in the body for receiving said inert member in a position adjacent to said diaphragm, said inert member including a flow channel configured to receive said plug, said plug movable between a first position and a second position wherein in said first position said plug is retained in said flow channel and thereby prevents fluid flow through said barrier and in said second position said plug is dislodged from said flow channel and thereby allows fluid flow through the barrier by passing through said flow channel and said flow aperture.

14. An elastomeric sealing piston, comprising:
    a resilient main body having a first side, a second side and a perimeter surface coupling said first side to said second side, said perimeter surface having a sealing ridge, said entire main body being generally cylindrical in shape;
    a pharmaceutically inert member;
    a cavity formed in the main body for receiving and retaining the entire inert member within the cavity, said inert member forming a substantial portion of said first side; and
    interlock means for mechanically securing the inert member within the cavity.

15. The piston of claim 14 wherein said inert member is molded into the main body, said inert member forming a needle channel and a needle guide to allow needle cannula access through said piston, said main body further having a recess disposed adjacent said needle guide to facilitate alignment of a needle cannula with said needle channel.

16. The piston of claim 14 wherein said insert has an open side and a needle-piercable closed side.

17. The piston of claim 14 wherein said insert has a channel to facilitate the passing of a needle cannula longitudinally through said main body and said insert.

18. An elastomeric sealing barrier for sealing an open end of a rigid container of the type having a radially outwardly facing outer surface at the open end, the barrier comprising a main body and an inert member, said main body having a circumferentially extending perimeter wall including an inner surface sized to engage the outer surface of the rigid container, and an end barrier extending from the perimeter wall across the open end of the container, the end barrier having an inner face facing into the rigid container and an outer face facing away from the rigid container, at least one of said inner and outer faces being a pharmaceutically inert face, the perimeter wall configured to form a fluid tight seal around the outer surface at the open end of said rigid container, the inert member coupled to the end barrier, the end barrier and inert member therewith configured to seal said open end of said container, the inert member acting as a substantial portion of the pharmaceutically inert face, said end barrier being coupled to a plug, said inert member further comprising a flow channel having a plug seat configured to receive said plug, said plug movable between a first position and a second position wherein in said first position said plug is retained in said flow channel and thereby prevents fluid flow through said end barrier and in said second position said plug is dislodged from said plug seat and thereby allows fluid flow through the flow channel to pass between the inner face and other face of said end barrier.

* * * * *